(12) United States Patent
Jeong et al.

(10) Patent No.: US 12,291,700 B2
(45) Date of Patent: May 6, 2025

(54) ORGAN-ON-A-CHIP AND A FABRICATION METHOD THEREOF (71) Applicant: INJE UNIVERSITY INDUSTRY-ACADEMIC COOPERATION FOUNDATION, Gimhae-si (KR)

(72) Inventors: Sehoon Jeong, Gimhae-si (KR); Dong-Jin Jang, Gimhae-si (KR); Sang Eun Im, Gimhae-si (KR); Min Young Choi, Gimhae-si (KR); Jin A Yoon, Gimhae-si (KR)

(73) Assignee: INJE UNIVERSITY INDUSTRY-ACADEMIC COOPERATION FOUNDATION, Gimhae-si (KR)

( * ) Notice: Subject to any disclaimer, the term of this patent is extended or adjusted under 35 U.S.C. 154(b) by 749 days.

(21) Appl. No.: 17/616,435

(22) PCT Filed: Aug. 28, 2021

(86) PCT No.: PCT/KR2021/011391
§ 371 (c)(1),
(2) Date: Dec. 3, 2021

(87) PCT Pub. No.: WO2022/045780
PCT Pub. Date: Mar. 3, 2022

(65) Prior Publication Data
US 2022/0290081 A1 Sep. 15, 2022

(30) Foreign Application Priority Data
Aug. 25, 2020 (KR) .................. 10-2020-0106771

(51) Int. Cl.
*B01L 3/00* (2006.01)
*B01F 33/302* (2022.01)
(Continued)

(52) U.S. Cl.
CPC ............ *C12M 23/16* (2013.01); *C12M 23/38* (2013.01); *C12M 25/06* (2013.01); *C12M 29/04* (2013.01); *C12N 5/0679* (2013.01)

(58) Field of Classification Search
CPC ...... C12M 23/16; C12M 23/38; C12M 25/06; C12M 29/04; C12M 25/02; C12N 5/0679; C12N 5/0062
See application file for complete search history.

(56) References Cited

U.S. PATENT DOCUMENTS

2017/0058257 A1* 3/2017 Levner .................. C12M 29/10

FOREIGN PATENT DOCUMENTS

KR 10-1744663 B1 6/2017
KR 10-1985311 B1 6/2019
(Continued)

OTHER PUBLICATIONS

Jing, Bolin, et al. "Establishment and application of peristaltic human gut-vessel microsystem for studying host-microbial interaction." Frontiers in bioengineering and biotechnology 8 (2020): 272. (Year: 2020).*

(Continued)

*Primary Examiner* — Jennifer Wecker
*Assistant Examiner* — Oyeleye Alexander Alabi
(74) *Attorney, Agent, or Firm* — NKL Law; Jae Youn Kim (57) ABSTRACT The present disclosure relates to an organ-on-a-chip, and according to the present disclosure, the organ-on-a-chip includes a first layer having a first microfluidic channel to culture a first organ cell, a second layer having a second microfluidic channel, a third layer having a third microfluidic channel to culture a second organ cell, a first membrane to spatially separate the first microfluidic channel from the second microfluidic channel, and a second membrane to (Continued)

spatially separate the second microfluidic channel from the third microfluidic channel, thereby measuring the rate of absorption of a test drug into the first organ cell and the second organ cell at the same time.

2 Claims, 9 Drawing Sheets

(51) Int. Cl.
    *B01F 33/3033*    (2022.01)
    *B01L 7/00*    (2006.01)
    *C12M 1/00*    (2006.01)
    *C12M 1/12*    (2006.01)
    *C12M 3/06*    (2006.01)
    *C12N 5/071*    (2010.01)
    *C12Q 1/6848*    (2018.01)
    *C12Q 1/686*    (2018.01)
    *G01N 21/29*    (2006.01)

(56) References Cited

FOREIGN PATENT DOCUMENTS

KR    10-2020-0047538 A    5/2020
WO    2019/054500 A1    3/2019

OTHER PUBLICATIONS

Bolin Jing et al., "Establishment and Application of Peristaltic Human Gut-Vessel Microsystem for Studying Host-Microbial Interaction". Frontiers in Bioengineering and Biotechnology. vol. 8, Article 272. Mar. 31, 2020.

\* cited by examiner

ORGAN-ON-A-CHIP AND A FABRICATION METHOD THEREOF

TECHNICAL FIELD

The present disclosure relates to an organ-on-a-chip for testing the absorption of a drug into organ cells.

BACKGROUND ART

Most of drugs that can be taken orally are absorbed in the stomach and intestines. Absorption is the movement of a drug into the bloodstream after administration. Once the drug is absorbed, it circulates throughout the body, and the drug moves from the bloodstream to cells in specific tissues on which it acts, and distributes to the tissues across cell membranes. Subsequently, after the drug reaches the site of action through distribution and exerts its effects, it undergoes biotransformation or metabolism involving conversion into an inactive form for excretion, and excretion involving elimination of a byproduct of metabolism from the body takes place through organs such as kidney, intestines and lung.

The absorption in the stomach and intestines may be a first step of the complex process in which the orally administered drug reaches the site of action and exerts its effects, and except drugs that may be lost during movement throughout the body, and the initial absorption process is generally a main factor that determines the size of treatment effect.

To quantify the absorption of a drug into cells in the stomach or intestines, a permeability test using an organ-on-a-chip may be performed. It is necessary to measure the rate of drug absorption in a stomach cell culture organ-on-a-chip and the rate of drug absorption in an intestinal cell culture organ-on-a-chip, which causes procedural inconvenience of having to perform at least two tests. And as the number of tests increases, the time spent on testing increases, so it takes a considerable amount of time to perform the tests.

RELATED LITERATURES

Patent Literatures (Patent Literature) Korean Patent Application Publication No. 10-2020-0047538

DISCLOSURE

Technical Problem

The present disclosure is designed to solve the above-described problem, and therefore the present disclosure is directed to providing an organ-on-a-chip for measuring the rate of drug absorption into at least two organ cells.

Technical Solution

To achieve the above-described object, an organ-on-a-chip according to an embodiment of the present disclosure includes a first layer having a first microfluidic channel to culture a first organ cell, a second layer positioned below the first layer, the second layer having a second microfluidic channel, a third layer positioned below the second layer, the third layer having a third microfluidic channel to culture a second organ cell, a first membrane interposed between the first microfluidic channel and the second microfluidic channel to spatially separate the first microfluidic channel from the second microfluidic channel, and a second membrane interposed between the second microfluidic channel and the third microfluidic channel to spatially separate the second microfluidic channel from the third microfluidic channel.

Here, a reaction chamber including parts of the first microfluidic channel, the second microfluidic channel and the third microfluidic channel may be provided at a point or region at which the first microfluidic channel is positioned vertically above and the third microfluidic channel is positioned vertically below, in at least one point or region on the second microfluidic channel.

Here, when the first microfluidic channel, the second microfluidic channel and the third microfluidic channel are projected onto an imaginary plane parallel to the second layer, an angle between the first microfluidic channel and the second microfluidic channel may be equal to an angle between the second microfluidic channel and the third microfluidic channel.

Here, the first membrane interposed between the first microfluidic channel and the second microfluidic channel may become a substrate in which the first organ cell is cultured, and may be a porous flexible membrane through which a material moves from the second microfluidic channel to the first microfluidic channel.

Here, the second membrane interposed between the second microfluidic channel and the third microfluidic channel may become a substrate in which the second organ cell is cultured, and may be a porous flexible membrane through which a material moves from the second microfluidic channel to the third microfluidic channel.

Here, the organ-on-a-chip may further include a cover substrate positioned on the first layer to cover at least part of an upper surface of the first layer.

Here, the organ-on-a-chip may further include a base substrate positioned below the third layer to cover at least part of a lower surface of the third layer.

Here, the cover substrate may have a first inlet in communication with the first microfluidic channel to inject a predetermined drug or culture medium into an end of the first microfluidic channel.

Here, the cover substrate may have a second inlet in communication with the second microfluidic channel to inject the predetermined drug or culture medium into an end of the second microfluidic channel.

Here, the cover substrate may have a third inlet in communication with the third microfluidic channel to inject the predetermined drug or culture medium into at an end of the third microfluidic channel.

To achieve the above-described object, a method for fabricating an organ-on-a-chip according to an embodiment of the present disclosure includes a layer formation step of forming each of a first layer having a first microfluidic channel, a second layer having a second microfluidic channel and a third layer having a third microfluidic channel using polydimethylsiloxane (PDMS), and a layer connection step of connecting the first layer, the second layer and the third layer with a first membrane interposed between the first layer and the second layer formed in the layer formation step and a second membrane interposed between the second layer and the third layer.

Here, the method for fabricating an organ-on-a-chip may further include, after the layer connection step, a cell culture step of culturing a first organ cell in the first microfluidic channel using the first membrane as a substrate and a second organ cell in the third microfluidic channel using the second membrane as a substrate.

Here, the layer connection step may include connecting a cover substrate and a base substrate to an upper surface of the first layer and a lower surface of the third layer.

Advantageous Effects

The organ-on-a-chip according to an embodiment of the present disclosure can measure the rate of drug absorption into at least two organ cells at the same time, thereby reducing the time spent on testing and enhancing the drug absorption test efficiency.

BEST MODE

Hereinafter, the preferred embodiments will be described with reference to the accompanying drawings for a full and thorough understanding of the present disclosure.

The present disclosure may have a variety of modifications and include many embodiments, and particular embodiments are shown in the drawings and described in detail. However, this is not intended to limit the present disclosure to the particular embodiments, and should be understood as including all modifications, equivalents or substitutes within the spirit and scope of the present disclosure.

The terms "first", "second" and the like may be used to describe various elements, but the elements should not be limited by the terms. These terms are used to distinguish one element from another. For example, a first element may be referred to as a second element, and likewise, a second element may be referred to as a first element without departing from the scope of protection of the present disclosure. The term "and/or" includes a combination of items related to the plural form or any of the items.

It will be understood that when an element is referred to as being "connected to" or "coupled to" another element, it can be directly connected or coupled to the other element, but intervening elements may be present between them. In contrast, it will be understood that when an element is referred to as being "directly connected to" or "directly coupled to" another element, there are no intervening elements between them.

The terminology used herein is for the purpose of describing particular embodiments only and is not intended to be limiting of the present disclosure. As used herein, the singular forms include the plural forms as well, unless the context clearly indicates otherwise. It should be understood that the term "comprises" or "includes" when used in this specification, specifies the presence of stated features, integers, steps, operations, elements, components or a combination thereof, but does not preclude the presence or addition of one or more other features, integers, steps, operations, elements, components or a combination thereof.

Unless otherwise defined, all terms including technical and scientific terms used herein have the same meaning as commonly understood by those skilled in the art. The terms, such as those defined in commonly used dictionaries, should be interpreted as having a meaning that is consistent with their meaning in the context of the relevant art, and will not be interpreted in an idealized or overly formal sense unless expressly so defined herein.

Hereinafter, the preferred embodiments of the present disclosure will be described in more detail with reference to the accompanying drawings. In describing the present disclosure, for easy understanding of the present disclosure, like reference signs are used for like elements in the drawings and overlapping descriptions of like elements are omitted herein.

Figure 1:
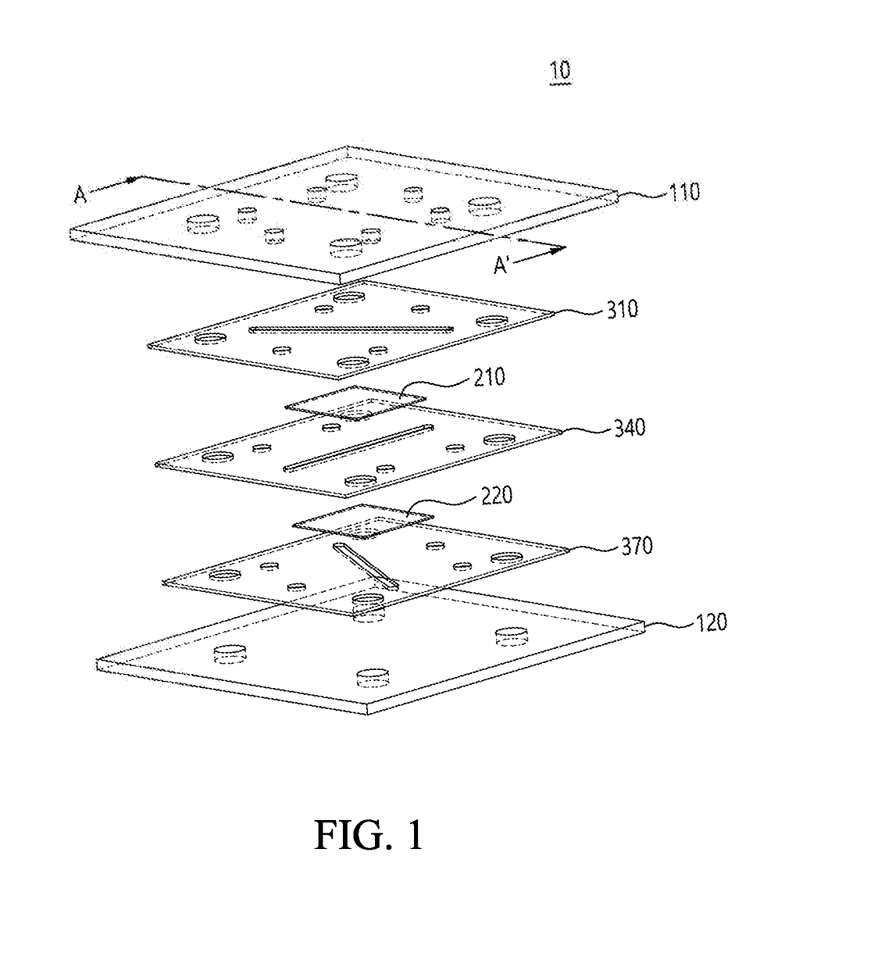
FIG. 1 is an exploded perspective view schematically showing an organ-on-a-chip according to an embodiment of the present disclosure.
Figure 2:
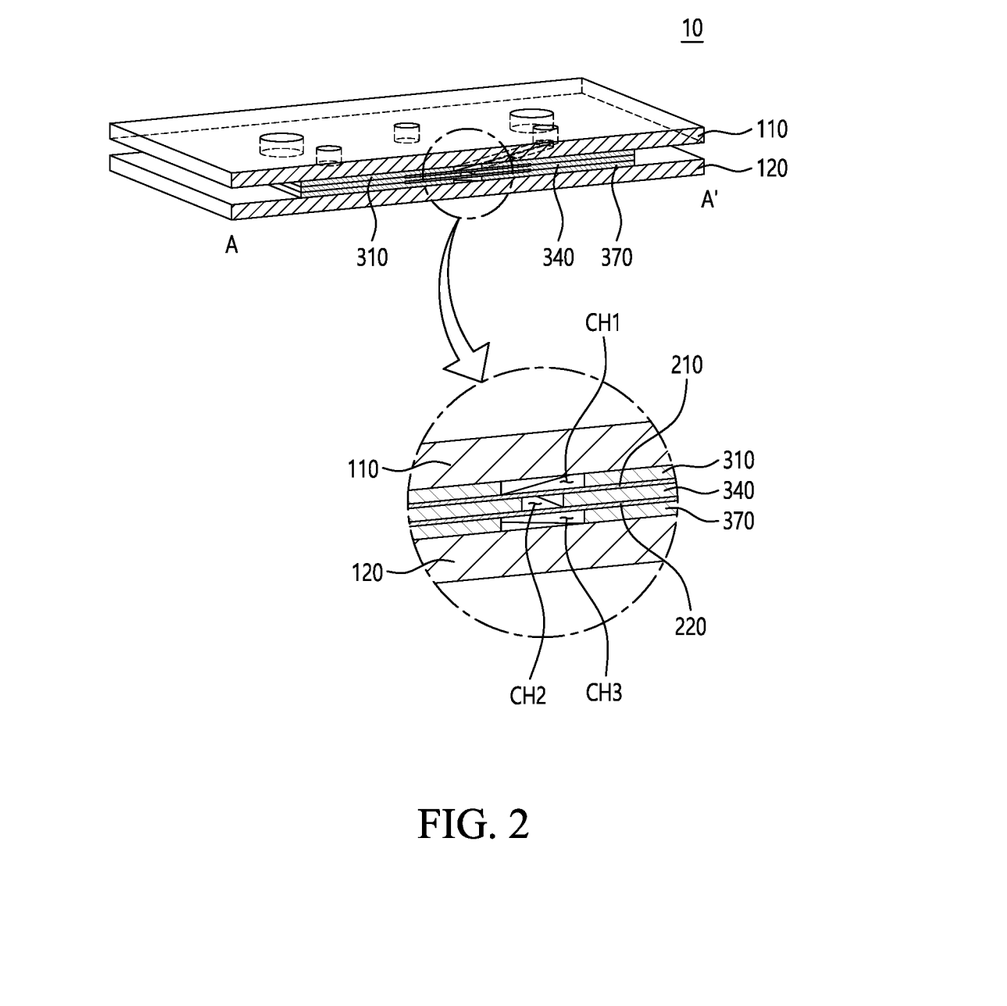
FIG. 2 is a side cross-sectional view schematically showing an organ-on-a-chip according to an embodiment of the present disclosure.

FIG. 1 is an exploded perspective view schematically showing an organ-on-a-chip according to an embodiment of the present disclosure, and FIG. 2 is a side cross-sectional view schematically showing a side cross section of the organ-on-a-chip according to an embodiment of the present disclosure.

Referring to FIGS. 1 and 2, the organ-on-a-chip 10 according to an embodiment of the present disclosure includes a first layer 310, a second layer 340, a third layer 370, a first membrane 210 and a second membrane 220, and may further include a base substrate 120 and a cover substrate 110.

As shown in the drawings in its entirety, the organ-on-a-chip 10 includes the second layer 340 below the first layer 310, and the third layer 370 below the second layer 340. Additionally, the first membrane 210 is interposed between the first layer 310 and the second layer 340, and the second membrane 220 is interposed between the second layer 340 and the third layer 370. Here, the cover substrate 110 covers the upper surface of the first layer 310, and the base substrate 120 serving as a base is provided on the lower surface of the third layer 370.

Hereinafter, the organ-on-a-chip will be described based on FIGS. 1 and 2 with further reference to FIGS. 3 to 8 in a sequential order.

Figure 3:
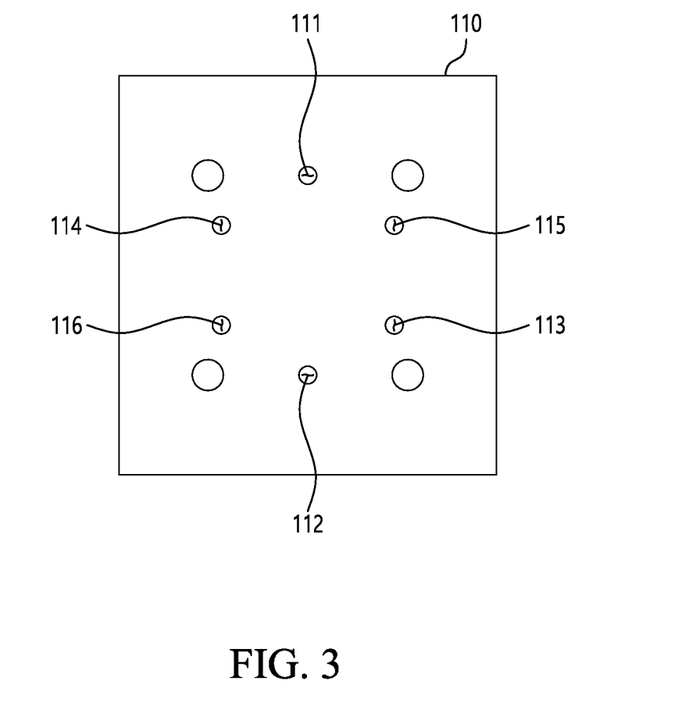
FIG. 3 is a top view schematically showing a cover substrate of an organ-on-a-chip according to an embodiment of the present disclosure.

FIG. 3 is a top view schematically showing the top side of the cover substrate of the organ-on-a-chip according to an embodiment of the present disclosure.

Referring further to FIG. 3, the cover substrate 110 of the organ-on-a-chip 10 according to an embodiment of the present disclosure is positioned on the first layer 310 and covers at least part of the upper surface of the first layer 310. The cover substrate 110 may be made of polycarbonate, but is not limited thereto.

Additionally, the cover substrate 110 includes a first inlet 115 in communication with a first microfluidic channel CH1 of the first layer 310 as described below to inject a predetermined drug or culture medium into one end of the first microfluidic channel, a second inlet 111 in communication with a second microfluidic channel CH2 of the second layer 340 to inject the predetermined drug or culture medium into one end of the second microfluidic channel CH2, and a third inlet 113 in communication with a third microfluidic channel CH3 of the third layer 370 to inject the predetermined drug or culture medium into one end of the third microfluidic channel CH3.

The culture medium or the predetermined drug may be injected through the first inlet 115, the second inlet 111 and the third inlet 113.

Additionally, the cover substrate 110 includes a first outlet 116 that may be in communication with the first inlet 115 through the first microfluidic channel CH1, a second outlet 112 that may be in communication with the second inlet 111 through the second microfluidic channel CH2, and a third outlet 114 that may be in communication with the third inlet 113 through the third microfluidic channel CH3.

Accordingly, the drug or culture medium injected into the first inlet 115 may enter the first microfluidic channel CH1, move along the first microfluidic channel CH1 and exit through the first outlet 116. Additionally, the drug or culture medium injected into the second inlet 111 may enter the first microfluidic channel CH1, move along the first microfluidic channel CH1 and exit through the second outlet 112.

Additionally, the drug or culture medium injected into the third inlet 113 may enter the first microfluidic channel CH1, move along the first microfluidic channel CH1 and exit through the third outlet 114.

The first layer 310 is positioned below the cover substrate 110 through connection to attach the first layer 310 to the lower surface of the cover substrate 110.

Figure 4:
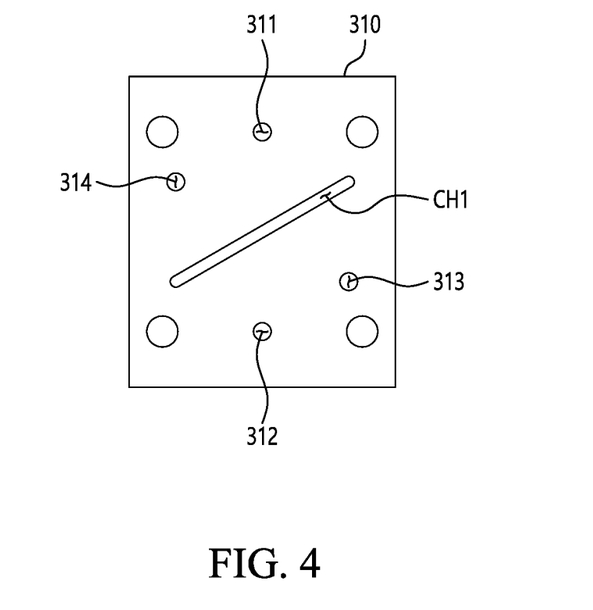
FIG. 4 is a top view schematically showing a first layer of an organ-on-a-chip according to an embodiment of the present disclosure.

FIG. 4 is a top view schematically showing the first layer 310 of the organ-on-a-chip according to an embodiment of the present disclosure.

Referring further to FIG. 4, the first layer 310 has the first microfluidic channel CH1 with a predetermined length to culture a first organ cell.

Here, the first organ cell may include, for example, a stomach cell or an intestinal cell, but it is obvious that cells in other organs may be applied. Additionally, the material of the first layer 310 may include polydimethylsiloxane (PDMS).

The first layer 310 has the first microfluidic channel CH1 with the predetermined length in the shape of a hole or groove to culture the first organ cell. A hole is illustrated by way of example.

The top of the first microfluidic channel CH1 is covered by the cover substrate 110 connected to the upper surface of the first layer 310, and is connected in communication with the first inlet 115 and the first outlet 116 provided in the cover substrate 110.

Additionally, when the first microfluidic channel CH1 is formed in the shape of a hole, the bottom of the first microfluidic channel CH1 is covered by the upper surface of the second layer 340, and is spatially separated by the first membrane 210 at a point or region at which the second microfluidic channel CH2 is positioned vertically below.

The first layer 310 has a second inlet 311 and a third inlet 313, and also has a second outlet 312 and a third outlet 314. When the first layer 310 and the cover substrate 110 are connected, the second inlet 311 formed in the first layer 310 is in communication with the second inlet 111 provided in the cover substrate 110. The third inlet 313 of the first layer 310 is in communication with the third inlet 113 of the cover substrate 110. The second outlet 312 and the third outlet 314 of the first layer 310 are in communication with the second outlet 112 and the third outlet 114 of the cover substrate 110, respectively.

Figure 5:
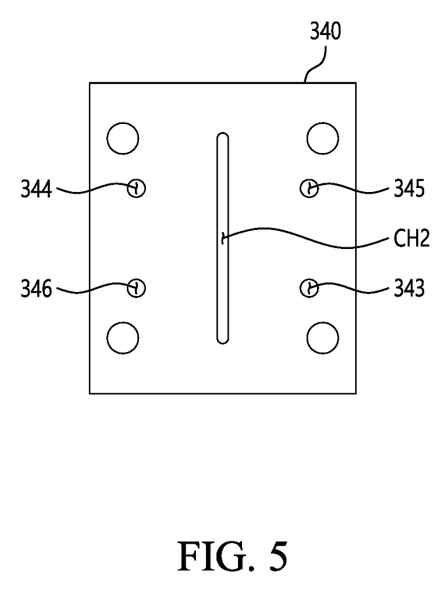
FIG. 5 is a top view schematically showing a second layer of an organ-on-a-chip according to an embodiment of the present disclosure.

FIG. 5 is a top view schematically showing the second layer 340 of the organ-on-a-chip according to an embodiment of the present disclosure.

Referring further to FIG. 5, the second layer 340 positioned below the first layer 310 has the second microfluidic channel CH2 with a predetermined length.

Additionally, the material of the second layer 340 may include polydimethylsiloxane (PDMS).

The second layer 340 has the second microfluidic channel CH2 with the predetermined length in the shape of a hole or groove to measure the rate or amount of drug absorption into the first organ cell or a second organ cell. The second microfluidic channel CH2 formed in the second layer 340 in the shape of a hole is illustrated by way of example.

Additionally, the second organ cell may be a cell of the same type as the first organ cell, but may be a different type of organ cell. For example, when the first organ cell is a stomach cell, an intestinal cell may be used as the second organ cell, but it is obvious that cells in other organs may be applied.

The top of the second microfluidic channel CH2 is covered by the first layer 310 connected to the upper surface of the second layer 340 or the first membrane 210, and is connected in communication with the second inlet 111, 311 and the second outlet 112, 312 provided in each of the cover substrate 110 and the first layer 310.

Additionally, when the second microfluidic channel CH2 is formed in the shape of a hole, the bottom of the second microfluidic channel CH2 is covered by the upper surface of the third layer 370 or the second membrane 220, and is spatially separated by the second membrane 220 at a point or region at which the third microfluidic channel CH3 is positioned vertically below.

The second layer 340 has a third inlet 343, and also has a third outlet 344. When the first layer 310 and the second layer 340 are connected, the third inlet 343 formed in the second layer 340 is in communication with the third inlets 113, 313 provided in the cover substrate 110 and the first layer 310. Likewise, the third outlet 344 formed in the second layer 340 is communication with the third outlets 114, 314 provided in the cover substrate 110 and the first layer 310.

Additionally, the first membrane 210 is interposed between the first microfluidic channel CH1 and the second microfluidic channel CH2 to spatially separate the first microfluidic channel CH1 from the second microfluidic channel CH2.

The first membrane 210 interposed between the first microfluidic channel CH1 and the second microfluidic channel CH2 becomes a substrate in which the first organ cell is cultured, and is preferably a porous flexible membrane through which a material can move from the second microfluidic channel CH2 to the first microfluidic channel CH1.

Accordingly, the first microfluidic channel CH1 and the second microfluidic channel CH2 may interact with the first membrane 210, which is a porous flexible membrane, interposed therebetween, and the first organ cell placed in a culture environment composed of the first membrane 210 and the first microfluidic channel CH1 may absorb the drug injected into the second microfluidic channel CH2.

Figure 6:
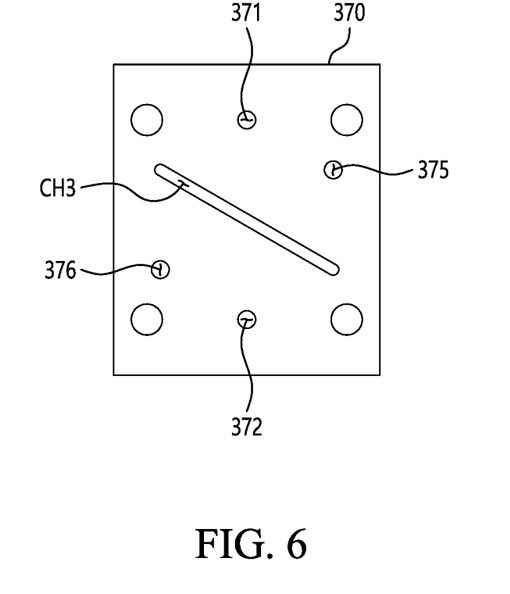
FIG. 6 is a top view schematically showing a third layer of an organ-on-a-chip according to an embodiment of the present disclosure.

FIG. 6 is a top view schematically showing the third layer 370 of the organ-on-a-chip according to an embodiment of the present disclosure.

Referring further to FIG. 6, the third layer 370 has the third microfluidic channel CH3 with a predetermined length to culture the second organ cell.

Here, the second organ cell may include, for example, a stomach cell or an intestinal cell, but it is obvious that cells in other organs may be applied. When the first organ cell is a stomach cell, the second organ cell may be an intestinal cell. Additionally, the material of the third layer 370 may include polydimethylsiloxane (PDMS).

The third layer 370 has the third microfluidic channel CH3 with the predetermined length in the shape of a hole or groove to culture the second organ cell. A hole is illustrated by way of example.

Here, the second organ cell may be a cell of the same type as the first organ cell as mentioned above, but may be a different type of organ cell. For example, when the first organ cell is a stomach cell, an intestinal cell may be used as the second organ cell, but this is provided by way of example, and cells in other organs may be applied.

The top of the third microfluidic channel CH3 is covered by the second layer 340 connected to the upper surface of the third layer 370 or the second membrane 220, and is connected in communication with the third inlet 113, 313, 343 and the third outlet 114, 314, 344 provided in each of the cover substrate 110, the first layer 310 and the second layer 340.

Additionally, when the third microfluidic channel CH3 is formed in the shape of a hole, the bottom of the third microfluidic channel CH3 is covered by the upper surface of the base substrate 120 to prevent exposure, and is spatially separated by the second membrane 220 at a point or region at which the second microfluidic channel CH2 is positioned vertically above.

The second membrane 220 is interposed between the second microfluidic channel CH2 and the third microfluidic channel CH3 to spatially separate the second microfluidic channel CH2 from the third microfluidic channel CH3.

The second membrane 220 interposed between the second microfluidic channel CH2 and the third microfluidic channel CH3 becomes a substrate in which the second organ cell is cultured, and is preferably a porous flexible membrane through which a material can move from the second microfluidic channel CH2 to the third microfluidic channel CH3.

Accordingly, the second microfluidic channel CH2 and the third microfluidic channel CH3 may interact with the second membrane 220, which is a porous flexible membrane, interposed therebetween, and the second organ cell placed in a culture environment composed of the second membrane 220 and the third microfluidic channel CH3 may absorb the drug injected into the second microfluidic channel CH2.

Figure 7:
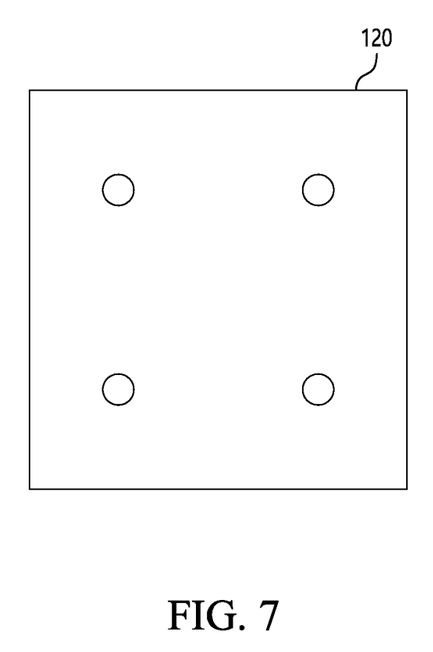
FIG. 7 is a top view schematically showing a base substrate of an organ-on-a-chip according to an embodiment of the present disclosure.

FIG. 7 is a top view schematically showing the base substrate of the organ-on-a-chip according to an embodiment of the present disclosure.

Referring further to FIG. 7, the base substrate 120 is a substrate that is positioned below the third layer 370 and covers at least part of the lower surface of the third layer 370.

The base substrate 120 may be made of polycarbonate, but is not limited thereto.

The base substrate 120 may serve as a base to support the first to third layers 310, 340, 370, the first membrane 210, the second membrane 220 and the cover substrate 110.

Furthermore, the base substrate 120 is connected and attached to the lower surface of the third layer 370. Accordingly, when the third microfluidic channel CH3 of the third layer 370 is formed in the shape of a hole, the base substrate 120 serves to cover the third microfluidic channel CH3 to prevent exposure. Furthermore, the base substrate 120 serves to cover the inlet or the outlet provided in the third layer 370.

Figure 8:
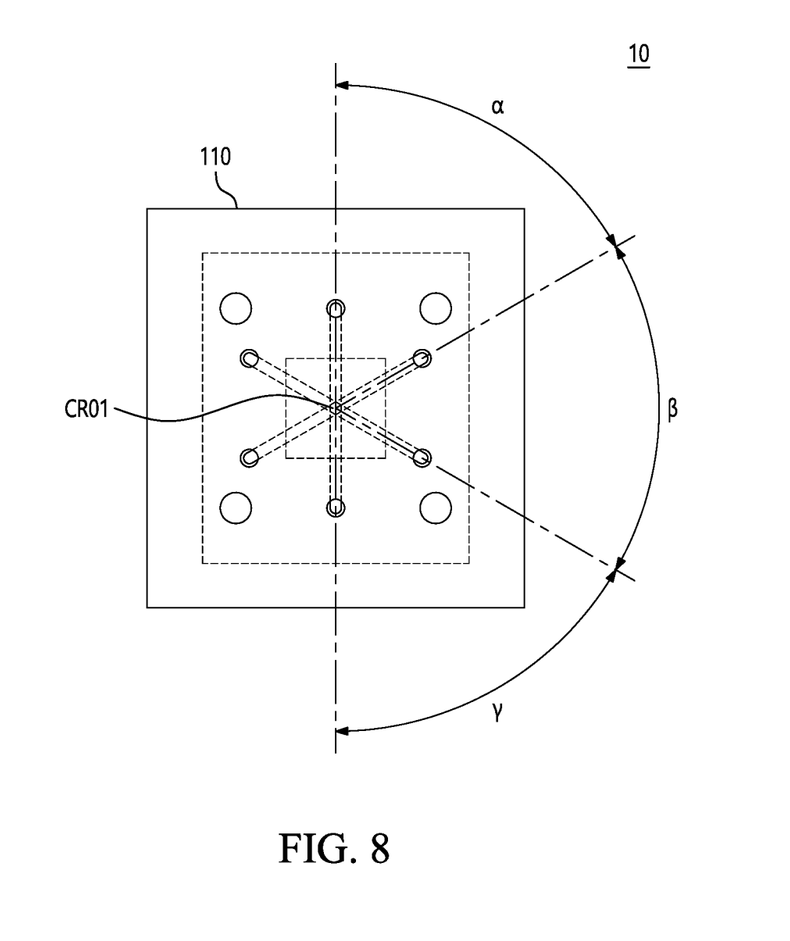
FIG. 8 is a top view schematically showing an organ-on-a-chip according to an embodiment of the present disclosure.

FIG. 8 is a top view schematically showing the organ-on-a-chip according to an embodiment of the present disclosure.

Referring further to FIG. 8, as shown in FIG. 8, when the first microfluidic channel CH1, the second microfluidic channel CH2 and the third microfluidic channel CH3 are projected onto an imaginary plane parallel to the second layer 340, it is preferred that an angle $\alpha$ between the first microfluidic channel CH1 and the second microfluidic channel CH2 is equal to an angle $\gamma$ between the second microfluidic channel CH2 and the third microfluidic channel CH3.

More preferably, an angle $\beta$ between the first microfluidic channel CH1 and the third microfluidic channel CH3 is also equal the angle $\alpha$ and the angle $\gamma$. When the three angles $\alpha$, $\beta$, $\gamma$ between the first microfluidic channel CH1 to the third microfluidic channel CH3 are equal, it is possible to provide the maximum distance or spacing between the inlets or the outlets provided at the ends of the three microfluidic channels, thereby allowing a user to perform the testing task more conveniently.

The first microfluidic channel CH1, the second microfluidic channel CH2 and the third microfluidic channel CH3 are not limited to the straight line shape as shown in the drawings, and the microfluidic channel may be formed in a bent shape at any angle at a certain point according to design requirements.

Additionally, it is preferred that a reaction chamber CR01 including parts of each of the first microfluidic channel CH1, the second microfluidic channel CH2 and the third microfluidic channel CH3 is provided at a point or region at which a point or region of the first microfluidic channel CH1 is positioned vertically above and a point or region of the third microfluidic channel CH3 is positioned vertically below, in at least one point or region on the second microfluidic channel CH2.

The reaction chamber CR01 includes a part of the first microfluidic channel CH1, a part of the second microfluidic channel CH2 and a part of the third microfluidic channel CH3 on a vertical line. Additionally, as shown in the partial enlarged diagram of FIG. 2, it is possible to spatially separate the microfluidic channels CH1, CH2, CH3 by the first membrane 210 and the second membrane 220.

In the reaction chamber CR01, it is possible to test the amount of absorption of the drug injected through the second microfluidic channel CH2 into the first organ cell and the second organ cell at the same time.

The organ-on-a-chip 10 according to the present disclosure forms an independent environment for each microfluidic channel. The first membrane 210 and the second membrane 220 are porous in about a few micro-scale pore size, and by the membranes 210, 220, it is possible to spatially separate each microfluidic channel and enable interaction such as absorption or desorption of a material between each microfluidic channel CH1, CH2, CH3.

Subsequently, a method for fabricating an organ-on-a-chip according to an embodiment of the present disclosure will be described with further reference to FIG. 9.

Figure 9:
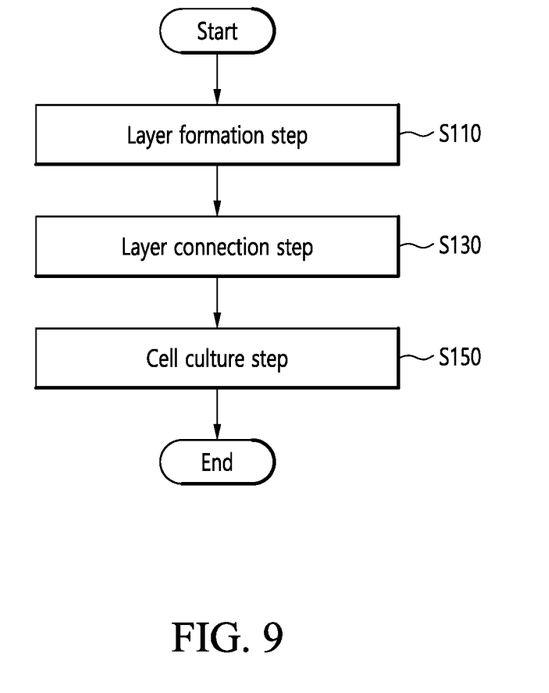
FIG. 9 is a flowchart schematically showing a method for fabricating an organ-on-a-chip according to an embodiment of the present disclosure.

FIG. 9 is a flowchart schematically showing the method for fabricating an organ-on-a-chip according to an embodiment of the present disclosure.

Referring further to FIG. 9, the method for fabricating an organ-on-a-chip according to an embodiment of the present disclosure includes a layer formation step (S110) and a layer connection step (S130), and may further include a cell culture step (S150).

In the layer formation step (S110), each of the first layer 310 having the first microfluidic channel CH1, the second layer 340 having the second microfluidic channel CH2, and the third layer 370 having the third microfluidic channel CH3 is formed using polydimethylsiloxane (PDMS). The method for forming the layer using PDMS to form the microfluidic channel is well known and its detailed description is omitted herein.

Subsequently, in the layer connection step (S130), the first layer 310, the second layer 340 and the third layer 370 are connected with the first membrane 210 interposed between the first layer 310 and the second layer 340 formed in the layer formation step (S110) and the second membrane 220 interposed between the second layer 340 and the third layer 370.

Here, as shown in FIG. 2 described above, it is preferred to connect the first layer 310, the second layer 340 and the third layer 370 so that the reaction chamber CR01 including parts of each of the first microfluidic channel CH1, the second microfluidic channel CH2 and the third microfluidic channel CH3 is positioned at a point or region at which a point or region of the first microfluidic channel CH1 is positioned vertically above, and a point or region of the third microfluidic channel CH3 is positioned vertically below, in at least one point or region on the second microfluidic channel CH2.

The reaction chamber CR01 includes a part of the first microfluidic channel CH1, a part of the second microfluidic channel CH2 and a part of the third microfluidic channel CH3 on a vertical line. Additionally, as shown in the partial enlarged diagram of FIG. 2, it is possible to spatially separate the micro fluidic channels CH1, CH2, CH3 by the first membrane 210 and the second membrane 220.

Here, the first layer 310, the second layer 340 and the third layer 370 may be connected using plasma.

Additionally, it is preferred to connect the cover substrate 110 and the base substrate 120 to the upper surface of the first layer 310 and the lower surface of the third layer 370.

After the layer connection step (S130), the cell culture step (S150) may be performed.

In the cell culture step (S150), the first organ cell is cultured in the first microfluidic channel CH1 using the first membrane 210 as a substrate and the second organ cell is cultured in the third microfluidic channel CH3 using the second membrane 220 as a substrate.

The culture medium may be supplied through the first microfluidic channel to culture the first organ cell, and the culture medium may be supplied through the third microfluidic channel to culture the second organ cell.

When the first organ cell and the second organ cell are cultured through the cell culture step (S150), a test may be performed to measure the amount of drug absorption.

As described above, according to the organ-on-a-chip of the present disclosure, it is possible to measure the rate of drug absorption into at least two organ cells at the same time, thereby reducing the time spent on testing and enhancing the drug absorption test efficiency.

Although the present disclosure has been hereinabove described in detail by the embodiment disclosed with reference to the accompanying drawings, the above-described embodiments have been described using the preferred embodiments of the present disclosure, so the present disclosure should not be understood as being limited to these embodiments, and the scope of protection of the present disclosure should be understood in the appended claims and their equivalent concept.

DETAILED DESCRIPTION OF MAIN ELEMENTS

| | |
|---|---|
| 10: Organ-on-a-chip | 110: Cover substrate |
| 120: Base substrate | 210: First membrane |
| 220: Second membrane | 310: First layer |
| 340: Second layer | 370: Third layer |
| CH1: First microfluidic channel | CH2: Second microfluidic channel |
| CH3: Third microfluidic channel | CR01: Reaction chamber |

The invention claimed is:

1. An organ-on-a-chip, comprising:
a first layer having a first microfluidic channel to culture a first organ cell, wherein the first microfluidic channel is formed in a shape of a straight hole with a predetermined length;
a second layer positioned below the first layer, the second layer having a second microfluidic channel to measure a rate or amount of drug absorption into the first organ cell or a second organ cell, wherein the second microfluidic channel is formed in a shape of a straight hole with a predetermined length;
a third layer positioned below the second layer, the third layer having a third microfluidic channel to culture the second organ cell, wherein the third microfluidic channel is formed in a shape of a straight hole with a predetermined length;
a first membrane interposed between the first microfluidic channel and the second microfluidic channel to spatially separate the first microfluidic channel from the second microfluidic channel;
a second membrane interposed between the second microfluidic channel and the third microfluidic channel to spatially separate the second microfluidic channel from the third microfluidic channel;
a cover substrate disposed on an upper side of the first layer and covering at least a portion of the upper side of the first layer; and
a base substrate disposed on a lower side of the third layer and covering at least a portion of the lower side of the third layer,
wherein a reaction chamber including a part of the first microfluidic channel, a part of the second microfluidic channel and a part of the third microfluidic channel is provided in at least one point or region of the second microfluidic channel at which the first microfluidic channel is positioned vertically above thereof and the third microfluidic channel is positioned vertically below thereof,
wherein, when the first microfluidic channel, the second microfluidic channel, and the third microfluidic channel are projected onto an imaginary plane parallel to the second layer, an angle between the first microfluidic channel and the second microfluidic channel and an angle between the second microfluidic channel and the third microfluidic channel are formed to be equal,
wherein the first membrane, disposed between the first microfluidic channel and the second microfluidic channel, serves as a substrate for culturing the first organ cell, the first membrane being a porous flexible membrane through which a material can move from the second microfluidic channel to the first microfluidic channel, wherein the second membrane disposed between the second microfluidic channel and the third microfluidic channel, serves as a substrate for culturing the second organ cell, the second membrane being a porous flexible membrane through which a material can move from the second microfluidic channel to the third microfluidic channel, wherein the cover substrate includes a first inlet in communication with the first microfluidic channel to inject a predetermined drug or culture medium into an end of the first microfluidic channel, wherein the cover substrate includes a second inlet in communication with the second microfluidic channel to inject a predetermined drug or culture medium into an end of the second microfluidic channel, wherein the cover substrate includes a third inlet in communication with the third microfluidic channel to inject a predetermined drug or culture medium into an end of the third microfluidic channel, and wherein the reaction chamber tests the amount of absorption of the drug injected through the second microfluidic channel into the first organ cell or the second organ cell at the same time.

2. A method for fabricating an organ-on-a-chip, comprising:

forming each of a first layer having a first microfluidic channel to culture a first organ cell, the first microfluidic channel formed in a shape of a hole with a predetermined length, a second layer having a second microfluidic channel to measure a rate or amount of drug absorption into the first organ cell or a second organ cell, the second microfluidic channel formed in a shape of a hole with a predetermined length, and a third layer having a third microfluidic channel to culture the second organ cell, the third microfluidic channel formed in a shape of a hole with a predetermined length using polydimethylsiloxane (PDMS);

connecting the first layer, the second layer, and the third layer with a first membrane interposed between the first layer and the second layer and a second membrane interposed between the second layer and the third layer, wherein a cover substrate, which is made of polycarbonate, is connected with a base substrate at an upper surface of the first layer and a lower surface of the third layer; and culturing a first organ cell in the first microfluidic channel using the first membrane as a substrate and a second organ cell in the third microfluidic channel using the second membrane as a substrate, wherein the first membrane is a porous flexible membrane through which a material can move from the second microfluidic channel to the first microfluidic channel, wherein the second membrane is a porous flexible membrane through which a material can move from the second microfluidic channel to the third microfluidic channel, wherein a cover substrate, which is made of polycarbonate, is connected with a base substrate at an upper surface of the first layer and a lower surface of the third layer, wherein the cover substrate includes a first inlet in communication with the first microfluidic channel to inject a predetermined drug or culture medium into an end of the first microfluidic channel, wherein the cover substrate includes a second inlet in communication with the second microfluidic channel to inject a predetermined drug or culture medium into an end of the second microfluidic channel, and wherein the cover substrate includes a third inlet in communication with the third microfluidic channel to inject a predetermined drug or culture medium into an end of the third microfluidic channel, wherein a reaction chamber including a part of the first microfluidic channel, a part of the second microfluidic channel and a part of the third microfluidic channel is provided in at least one point or region on the second microfluidic channel at which the first microfluidic channel is positioned vertically above thereof and the third microfluidic channel is positioned vertically below thereof, wherein, when the first microfluidic channel, the second microfluidic channel, and the third microfluidic channel are projected onto an imaginary plane parallel to the second layer, an angle between the first microfluidic channel and the second microfluidic channel and an angle between the second microfluidic channel and the third microfluidic channel are formed to be equal, and wherein the reaction chamber tests the amount of absorption of the drug injected through the second microfluidic channel into the first organ cell or the second organ cell at the same time.

* * * * *